United States Patent
Shirley et al.

[11] Patent Number: 6,027,511
[45] Date of Patent: Feb. 22, 2000

[54] DIGITAL AMNIOTOME WITH DIRECTIONAL INDICATOR

[75] Inventors: Ben Shirley, Salt Lake City; Wayne D. Carlsen, West Jordan, both of Utah

[73] Assignee: Utah Medical Products, Inc., Midvale, Utah

[21] Appl. No.: 09/130,419

[22] Filed: Aug. 6, 1998

[51] Int. Cl.[7] .................................................. A61B 17/42
[52] U.S. Cl. ........................................ 606/125; 606/119
[58] Field of Search ...................... 606/119, 125; 128/844

[56] References Cited

U.S. PATENT DOCUMENTS

| | | | |
|---|---|---|---|
| 203,959 | 5/1878 | Townsend . | |
| 622,386 | 4/1899 | Perry . | |
| 693,554 | 2/1902 | Langstaff . | |
| 2,084,692 | 6/1937 | Little | 606/125 |
| 2,811,969 | 11/1957 | Shubert | 128/303 |
| 2,847,012 | 8/1958 | Eastman | 606/125 |
| 2,895,139 | 7/1959 | Compton | 2/161 |
| 3,062,212 | 11/1962 | Kravitz et al. | 128/253 |
| 3,126,890 | 3/1964 | Deming, Sr. | 128/361 |
| 3,362,408 | 1/1968 | Stocki et al. | 128/314 |
| 3,587,591 | 6/1971 | Satterwhite | 606/125 |
| 3,687,139 | 8/1972 | Poirier | 606/125 |
| 3,735,760 | 5/1973 | Vreeland, Jr. | 604/212 |
| 3,741,211 | 6/1973 | Vreeland, Jr. | 606/125 |
| 3,749,099 | 7/1973 | Cotey | 606/125 |
| 3,867,947 | 2/1975 | Schack | 128/361 |
| 4,198,985 | 4/1980 | Abel | 606/125 |
| 5,036,589 | 8/1991 | Heinrich | 30/298 |

FOREIGN PATENT DOCUMENTS

| | | | |
|---|---|---|---|
| WO 86/00212 | 1/1986 | WIPO | 606/125 |

*Primary Examiner*—Paul J. Hirsch
*Assistant Examiner*—Michael B. Priddy
*Attorney, Agent, or Firm*—Madson & Metcalf

[57] ABSTRACT

A digital amniotome with a directional indicator, having an elastomeric finger sheath configured to fit over a user's finger, and a membrane rupturing unit having a sharp-tipped element extending from a base. The sharp-tipped element is directionally oriented, such that it has a cutting edge for rupturing an amniotic membrane and a smooth edge. In one embodiment, the base is secured to the interior surface of the distal end of the finger sheath such that the sharp-tipped element passes through the opening in the distal end of said finger sheath. The base and/or the opening of the finger sheath are shaped to facilitate visual identification of the directional orientation of the sharp-tipped element. The finger sheath is color contrasted with the base to further facilitate visual identification of directional orientation of the sharp-tipped element. In another embodiment, the base is secured to the distal end of the finger sheath at its exterior surface, and the base is shaped to provide visual identification of the directional orientation of the sharp-tipped element.

20 Claims, 3 Drawing Sheets

DIGITAL AMNIOTOME WITH DIRECTIONAL INDICATOR

BACKGROUND

1. The Field of the Invention

This invention relates generally to a digital amniotome, and more particularly to a digital amniotome with a directional indicator to facilitate the orientation of an attached sharp-tipped element.

2. Technical Background

The amniotic membrane is the sac surrounding the fetus in a pregnant woman's womb. In order to hasten labor and delivery, it is often desirable to artificially break the amniotic membrane. To accomplish this, a membrane-rupturing device is often inserted into the cervix through the vagina. One method is to have the membrane-rupturing device either attached to a finger or integral with a surgical glove. Such device is introduced into the cervix via the finger. Several finger-attachment and surgical glove devices are known in the art for rupturing amniotic membranes. Preferably, such devices would allow the user to maintain finger-sensitivity—allowing determination of the proper location to rupture the membrane. Also, preferably, the device would not damage other membranes or tissues, it would be operable with a single finger, and it would be simple to manufacture and use.

A finger sheath device is known in the art that has a small, sharp-tipped element attached to the interior surface of the distal end of the finger-sheath. The sharp-tipped element of this device is directional, i.e., the sharp-tipped element has both a cutting edge and a smooth edge. However, because the element is small, and there are no directional indicators on the device, it is difficult for a user to determine the orientation of the sharp-tipped element. The device lacks directional indicators because the base upon which the element sits is round, the hole through which the sharp-tipped element extends is round, and the base is approximately the same color as the finger-sheath. If the device is not properly oriented on the user's finger, it is difficult or impossible to use correctly.

Several other more complicated devices are also known in the art. Many comprise surgical gloves having modifications or attachments for rupturing an amniotic membrane. One such device includes a surgical glove having a hook on one side of the long finger. The hook is normally retracted, but it is extendible by the index finger in order to rupture the amniotic membrane. This device is limited in its application and is relatively difficult to operate; it requires sufficient dilation of the cervical opening for the user to insert at least two fingers through the cervical opening, and it also requires that the user be able to maneuver the index finger to engage the hook and hold it in an extended position while rupturing the membrane.

Another surgical glove is known that has a flexible sheath along the back surface of the glove. The sheath includes a retractable, flexible blade that is enclosed in the sheath and is extendable via a button on the top of the sheath. The button must be pressed by an adjacent finger. This device is both complex to manufacture and is complicated to operate. It requires at least two fingers to operate, requiring one finger to press a button on top of another finger. Also, the blade may cause injury to other tissue upon removal from the cervix and vagina.

Yet another surgical glove includes a finger attachment having a tapered metal pin for rupturing membranes. Although the pin is positioned to minimize damage to other membranes, because the pin is always operable, i.e., it is neither retractable nor directionally oriented, damage to other membranes is risked. Furthermore, because the pin is metal, there would be manufacturing obstacles in securing a metal pin to an elastomeric surgical glove.

Although a simple surgical glove with a hard, cone-shaped element enclosing the tip of a finger is known, because the hard element entirely encloses the finger, the finger would have no sensitivity to touch during the procedure. Thus, the finger could not feel for the proper position to rupture the membrane. Also, because the sharp tip is not directionally oriented, but rather is cone-shaped, there would be a risk of damaging any other membrane or tissues that the end of the finger contacted.

In addition to surgical glove devices, many finger-attachment devices are also known in the art. For instance, a ring-like device is known with a guard adjacent to a recessed portion positioned over the pad of the fingertip. The recessed portion is resilient and has a sharp-tipped element that is deployed when pressure is applied to the guard. Although the device would allow finger-sensitivity for determining the appropriate rupturing location, the device would be relatively complex to both manufacture and operate.

Similarly, a finger sheath is known that is made of stiffly flexible material and has a recessed sharp-tipped element that is extendible upon finger flexion. Because the device is made with stiffly flexible material, it would not permit sufficient finger-sensitivity to ensure proper positioning of the device, thus damage to other membranes would be risked. Additionally, this device would be relatively complex to manufacture and operate due to the retractable sharp-tipped element.

It will be appreciated that it would be an advancement in the art to provide a digital amniotome with a directional indicator that facilitates the proper orientation of the directionally oriented sharp-tipped element. It would be a further advancement in the art to provide such a device that is also simple to manufacture and operate.

BRIEF SUMMARY AND OBJECTS OF THE INVENTION

The present invention provides a digital amniotome with a directional indicator for determining the proper orientation of directionally oriented sharp-tipped element. The invention includes a membrane rupturing unit having a directionally oriented sharp-tipped element extending from a base that is secured to the distal end of a finger sheath. The finger sheath is configured to fit over a user's finger and is made of thin, elastic material such as neoprene, latex, or silicone. The base is preferably shaped to permit the visual identification of the directional orientation of the sharp-tipped element. The shape of the base may be triangular, arrowhead, pointed or otherwise.

In one embodiment, a digital amniotome with the foregoing features is provided, but the base is secured to the interior surface of the distal end of the finger sheath and is visible from the exterior of the finger sheath through an opening formed in the distal end of the finger sheath. The opening may be shaped to permit the visual identification of the directional orientation of the sharp-tipped element. The shape of the opening may be triangular, arrowhead, pointed or otherwise. In a currently preferred embodiment, both the base and the opening in the finger sheath are shaped to permit visual identification of the directional orientation of the sharp-tipped element. Thus, the visual identification of the directional orientation of the sharp-tipped element is permitted both from the exterior surface of the finger sheath via the opening, and from the interior surface of the finger sheath via the base.

In another digital amniotome embodiment within the scope of the present invention the opening in the finger sheath is shaped with a directional orientation, but the base is not so shaped. Thus, the directional orientation of the sharp-tipped element can be determined from viewing the exterior surface of the distal end of the finger sheath, but not by viewing the interior surface.

In yet another embodiment, the base is secured to the exterior surface of the distal end of the finger sheath. Because the sharp-tipped element is attached to the outside surface of the finger sheath via the base, no opening in the finger sheath is required.

In all of the above embodiments, the visual identification of the directional orientation of the sharp-tipped element may be further facilitated through the use of a base that is color contrasted with the finger sheath.

The digital amniotome is preferably rolled prior to use such that it may be unrolled over a user's finger upon use. After being unrolled, the device is introduced into the cervix via the finger. The finger may be used to examine the woman in order to determine the proper location for rupturing the amniotic membrane without damaging any other tissues or membranes. Once the proper location is determined, the directionally oriented sharp-tipped element may be positioned such that pressure combined with finger movement produced by finger flexion or curling will expose the cutting edge of the sharp-tipped element to the amniotic membrane, thus rupturing the amniotic membrane. The device can then be removed from the cervix and vagina without damaging other membranes or tissues.

BRIEF DESCRIPTION OF THE DRAWINGS

A more particular description of the invention briefly described above will be rendered by reference to the appended drawings. Understanding that these drawings only provide information concerning typical embodiments of the invention and are not therefore to be considered limiting of its scope, the invention will be described and explained with additional specificity and detail through the use of the accompanying drawings, in which.

DETAILED DESCRIPTION

Figure 1:
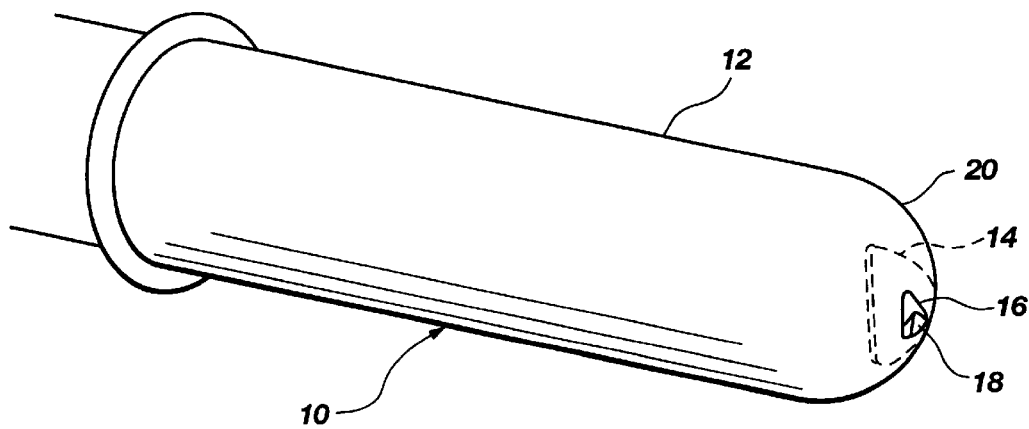
FIG. 1 is a perspective view of the digital amniotome showing the device as it appears unrolled over the user's finger and ready for use.

Reference is now made to the figures wherein like parts are referred to by like numerals throughout. With reference to FIG. 1, the present invention is a digital amniotome 10 having a directional indicator for rupturing an amniotic membrane. The digital amniotome 10 comprises a finger sheath 12 with an opening 16, and a directionally oriented sharp-tipped element 18 attached to a base 14. The base 14 is attached to the distal end 20 of the finger sheath 12.

The finger sheath 12 is made of a thin, elastomeric material suitable for medical use. The finger sheath 12 is sized and configured to fit snugly over a user's finger. The finger sheath 12 typically has a length ranging from about 2.3 inches to about 2.7 inches, with a length of about 2.5 inches being currently preferred. The finger sheath 12 typically has an outside diameter ranging from about 0.55 inches to about 0.75 inches, with an outside diameter of about 0.65 inches being currently preferred. The elastomeric material may comprise, but is not limited to, neoprene, latex, or silicone. In a preferred embodiment, the finger sheath 12 is tinted yellow, tan, or white or retains its natural color.

Figure 2:
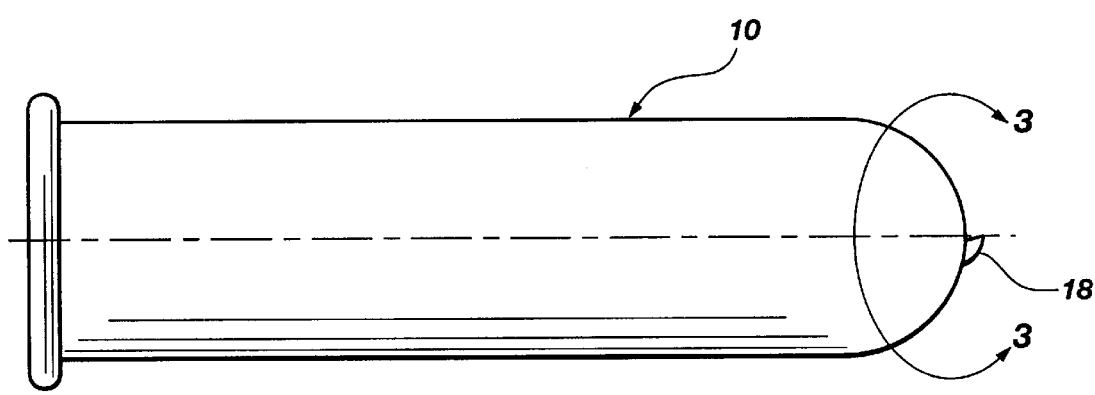
FIG. 2 is side view of the unrolled digital amniotome.
Figure 3:
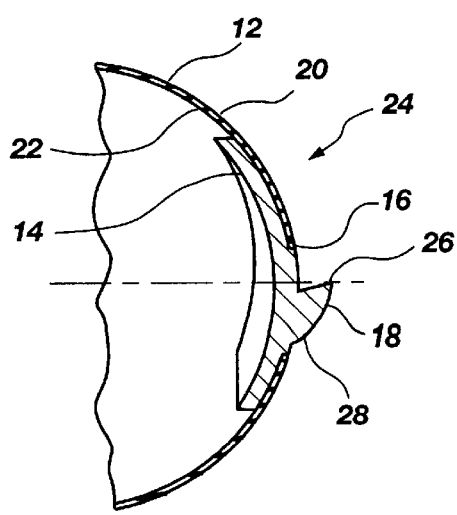
FIG. 3 is a partial cross-sectional view of the digital amniotome showing a detailed view of the distal end of the device.

With reference to FIGS. 1–3, the directionally oriented sharp-tipped element 18 is attached to the base 14. In one currently preferred embodiment, the sharp-tipped element 18 and the base 14 are integrally formed from a hard, thermoplastic material suitable for medical use. The thermoplastic material is preferably of sufficient hardness to maintain a sharp edge on the sharp-tipped element 18. Currently, the base 14 and the sharp-tipped element 18 are made of a polycarbonate that is injection molded to form the directionally oriented sharp-tipped element 18 integrally attached to the base 14.

In certain embodiments, the base 14 is shaped to facilitate the proper orientation of the directionally oriented sharp-tipped element 18. Also, the base 14 is preferably attached at the distal end 20 of the interior surface 22 of the finger sheath 12. The base 14 is positioned and affixed such that the sharp-tipped element 18 extends through the opening 16 in the finger sheath 12. One of ordinary skill in the art will appreciate that the method of affixing the base 14 to the finger sheath 12 will vary according to the materials used, and the materials used must be appropriate for medical applications. In a preferred embodiment, the base 14 is composed of an injection molded polycarbonate and is affixed to an elastomeric finger sheath 12 with glue, such as a cyanoacrylate glue.

A side view of the digital amniotome with a directional indicator 10 and a directionally oriented sharp-tipped element 18 is shown in FIG. 2.

With reference to FIG. 3, a membrane rupturing unit 24 is shown affixed to the distal end 20 of the finger sheath 12 in detailed cross section. In the embodiment shown, the base 14 is mounted to the interior surface 22 of the finger sheath 12 such that the base 14 is exposed through an opening 16 in the finger sheath 12, and the directionally oriented sharp-tipped element 18 extends through the opening 16 in the finger sheath 12. The sharp-tipped element 18 has both a cutting edge 26 and a smooth edge 28, thus the movement of the finger must be in the proper direction in order to rupture an amniotic membrane.

Figure 4:
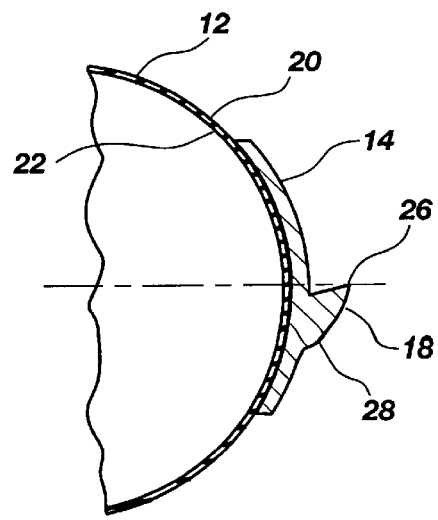
FIG. 4 is a partial cross-sectional view of the digital amniotome showing the base attached to the exterior surface of the finger sheath.

In an alternative embodiment, shown in FIG. 4, the base 14 is affixed directly to the outside surface of the finger sheath 12. Affixing the base 14 directly to the outside surface of the finger sheath 12 can reduce manufacturing costs because the opening 16 would not be needed. However, the base 14 is preferably affixed to the interior surface 22 of the finger sheath 12 to eliminate the possibility of the base 14 becoming dislodged and being left inside the patient.

Figure 5:
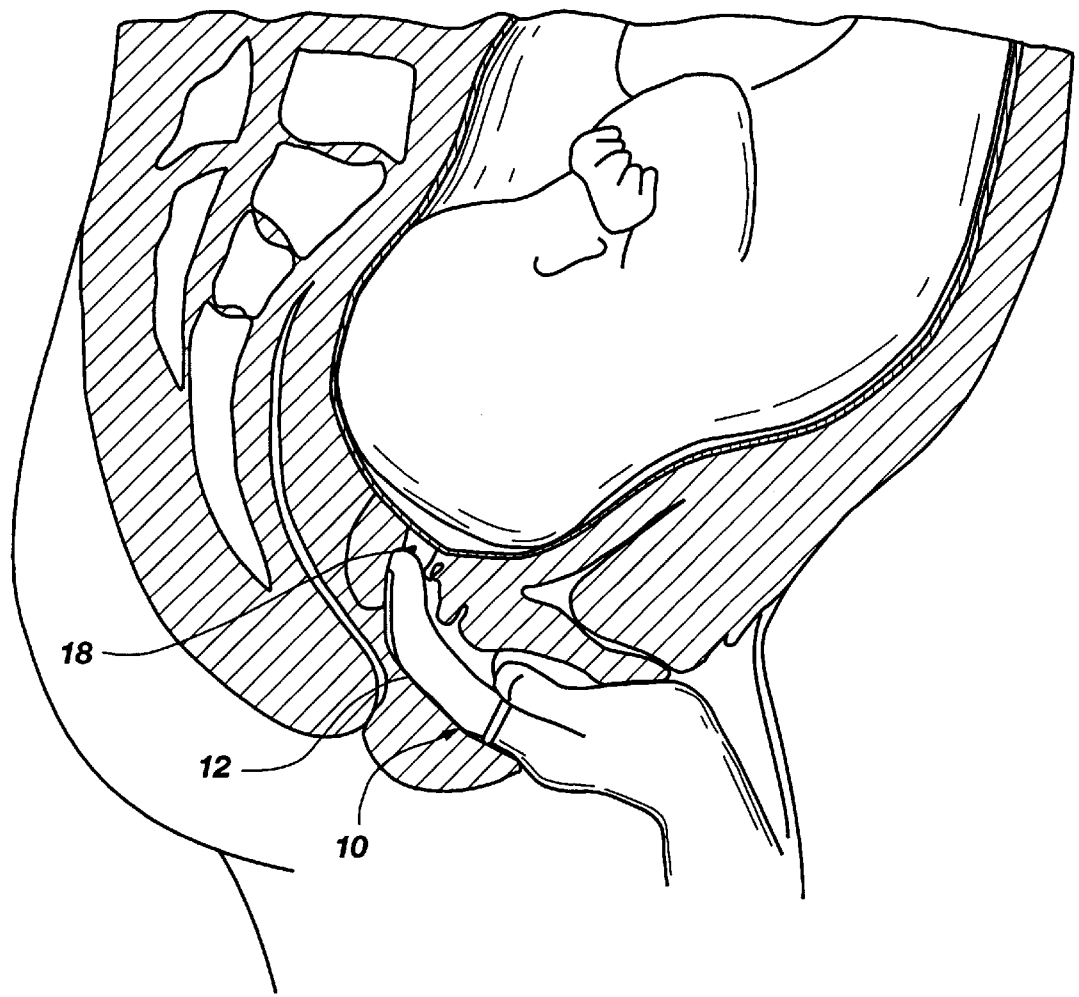
FIG. 5 is a sectional view of a pregnant female showing the digital amniotome positioned for use.

FIG. 5 shows the digital amniotome 10 having a directional indicator positioned for use. The digital amniotome 10 is preferably positioned over the user's finger such that the sharp-tipped element 18 is mounted on the distal end of a finger, and the cutting edge 26 of the sharp-tipped element 18 is oriented towards the palm. This finger is then inserted into a woman's cervical opening via the vagina, and positioned to contact the amniotic membrane. When the user combines finger movement produced by finger flexion or curling with finger pressure against amniotic membrane, the sharp-tipped element 18 will score the amniotic membrane causing it to rupture.

Figure 6:
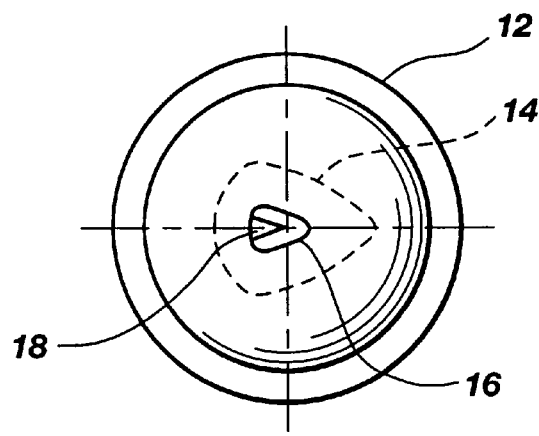
FIG. 6 is a frontal view of the rolled digital amniotome, prior to use.

FIG. 6 shows a frontal view of the rolled digital amniotome 10 prior to use. The opening 16 in the finger sheath 12 permits the directionally oriented sharp-tipped element 18 to protrude through the opening 16. Furthermore, the direction of the sharp-tipped element 18 can be determined by the shape of the opening 16. The shape must indicate direction and may comprise a shape such as a triangle, arrowhead, etc. FIG. 6 also demonstrates that a portion of the base 14 can be visualized through the opening 16. In certain embodiments, the base 14 is colored. Preferably, a dark color is used, such as black, navy blue, or dark brown. Therefore, the shape of the opening 16 in the finger sheath 12, and thus the proper orientation of the directionally oriented sharp-tipped element 18, can be readily determined by the contrast in color between the base 14 and the finger sheath 12.

Figure 7:
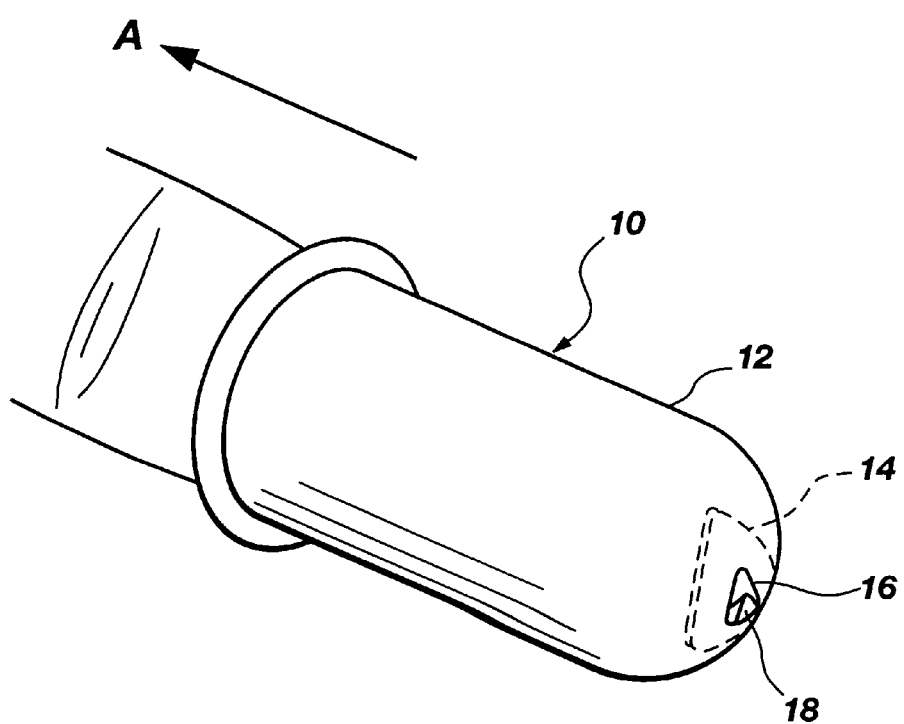
FIG. 7 is a perspective view of the partially unrolled digital amniotome showing the device being unrolled over a user's finger.

Finally, FIG. 7 shows the digital amniotome 10 having a directionally oriented sharp-tipped element 18 extending through the opening 16 in the finger sheath 12 as it is being unrolled in the direction of arrow A over a user's finger prior to use.

From the foregoing it can be appreciated that the present invention overcomes many of the limitations of the existing art. The present invention provides a digital amniotome with a directional indicator for the facile determination of the proper orientation of the directionally oriented sharp-tipped element. Moreover, the present invention is simple to manufacture and operate. Thus, the present invention represents an advancement in the art of amniotic membrane-rupturing devices.

The present invention may be embodied in other specific forms without departing from its spirit or essential characteristics. The described embodiments are to be considered in all respects only as illustrative and not restrictive. The scope of the present invention is, therefore, indicated by the appended claims rather than by the foregoing description. All changes which come within the meaning and range of equivalency of the claims are to be embraced within their scope.

What is claimed is:

1. A digital amniotome with a directional indicator, comprising:
    a finger sheath configured to fit over a user's finger, wherein said finger sheath has a distal end, an interior surface, and an exterior surface; and
    a membrane rupturing unit having a directionally oriented sharp-tipped element extending from a base, wherein the sharp-tipped element has a cutting edge configured to rupture an amniotic membrane, and wherein the base is secured to the distal end of the finger sheath, and wherein the base has a shape to facilitate visual identification of the directional orientation of the sharp-tipped element.

2. A digital amniotome as defined in claim 1, wherein the base has a triangular or arrowhead shape.

3. A digital amniotome as defined in claim 1, wherein the base has a pointed end.

4. A digital amniotome as defined in claim 1, wherein the finger sheath is made of neoprene.

5. A digital amniotome as defined in claim 1, wherein the finger sheath is made of latex.

6. A digital amniotome as defined in claim 1, wherein the finger sheath is made of silicone.

7. A digital amniotome as defined in claim 1, wherein the finger sheath is rolled up prior to use and is capable of being unrolled over the user's finger upon use.

8. A digital amniotome as defined in claim 1, wherein the finger sheath and the base have contrasting colors.

9. A digital amniotome as defined in claim 1, wherein the membrane rupturing unit is secured to the distal end of the finger sheath at its interior surface, and wherein the distal end of the finger sheath comprises an opening to allow passage of the sharp-tipped element through said opening.

10. A digital amniotome as defined in claim 9, wherein the opening in the finger sheath is shaped to facilitate visual identification of the directional orientation of the sharp-tipped element.

11. A digital amniotome as defined in claim 1, wherein the membrane rupturing unit is secured to the distal end of the finger sheath at its exterior surface.

12. A digital amniotome as defined in claim 1, wherein the finger sheath has a length ranging from about 2.3 inches to about 2.7 inches.

13. A digital amniotome as defined in claim 1, wherein the finger sheath has an outside diameter ranging from about 0.55 inches to about 0.75 inches.

14. A digital amniotome as defined in claim 1, wherein the membrane rupturing unit is made of hard thermoplastic material suitable for medical use.

15. A digital amniotome with a directional indicator, comprising:
    a finger sheath made of thin elastomeric material suitable for medical use configured to fit over a user's finger, wherein said finger sheath has a distal end, an interior surface, an exterior surface, and an opening at its distal end, and wherein said finger sheath has a length ranging from about 2.3 inches to about 2.7 inches and an outside diameter ranging from about 0.55 inches to about 0.75 inches; and
    a membrane rupturing unit having a directionally oriented sharp-tipped element extending from a base, wherein the sharp-tipped element has a cutting edge configured to rupture an amniotic membrane, and wherein the base is secured to the interior surface of the distal end of the finger sheath such that the sharp-tipped element passes through the opening in the distal end of the finger sheath, and wherein the base and the opening of the finger sheath are both shaped to facilitate visual identification of the directional orientation of the sharp-tipped element, and wherein the finger sheath and the base have contrasting colors.

16. A digital amniotome as defined in claim 15, wherein the finger sheath is rolled up prior to use and is capable of being unrolled over the user's finger upon use.

17. A digital amniotome as defined in claim 15, wherein the finger sheath is made of thin elastomeric material suitable for medical use.

18. A digital amniotome with a directional indicator, comprising:
    a finger sheath configured to fit over a user's finger, wherein said finger sheath has a distal end, an interior surface, an exterior surface, and an opening at its distal end; and
    a membrane rupturing unit having a directionally oriented sharp-tipped element with a cutting edge configured to rupture an amniotic membrane, wherein the sharp-tipped element extends from a base that is secured to the distal end of the interior surface of the finger sheath, and wherein the sharp-tipped element passes through the opening in the finger sheath, and wherein the opening is shaped to facilitate visual identification of the directional orientation of the sharp-tipped element.

19. A digital amniotome as defined in claim 18, wherein the finger sheath and the base have contrasting colors, and wherein the finger sheath has a length ranging from about 2.3 inches to about 2.7 inches and an outside diameter ranging from about 0.55 inches to about 0.75 inches, and wherein the finger sheath is rolled up prior to use and is capable of being unrolled over the user's finger upon use, and wherein the finger sheath is made of thin elastomeric material suitable for medical use.

20. A digital amniotome as defined in claim 19, wherein the base is shaped to facilitate visual identification of the directional orientation of the sharp-tipped element.

* * * * *